United States Patent [19]

Tuke et al.

[11] Patent Number: 5,219,362
[45] Date of Patent: Jun. 15, 1993

[54] KNEE PROSTHESIS

[75] Inventors: Michael A. Tuke, Guildford; Michael A. R. Freeman, London, both of England

[73] Assignee: Finsbury (Instruments) Limited, Chessington, United Kingdom

[21] Appl. No.: 832,002

[22] Filed: Feb. 6, 1992

[30] Foreign Application Priority Data

Feb. 7, 1991 [GB] United Kingdom ............... 9102633

[51] Int. Cl.[5] .............................................. A61F 2/38
[52] U.S. Cl. ...................................... 623/20; 623/16; 623/18
[58] Field of Search ................... 623/20, 16, 18, 66

[56] References Cited

U.S. PATENT DOCUMENTS

| | | | |
|---|---|---|---|
| 3,816,855 | 6/1974 | Saleh | 3/1 |
| 3,840,905 | 10/1974 | Deane | 3/1 |
| 4,178,641 | 12/1974 | Grundei | 3/1.911 |
| 4,207,627 | 6/1980 | Cloutier | 3/1.911 |
| 4,261,064 | 4/1981 | Helfet | 3/1.91 |
| 4,714,472 | 12/1987 | Averill | 623/20 |
| 4,728,332 | 3/1988 | Albrektsson | 623/20 |
| 4,963,152 | 10/1990 | Hofmann | 623/18 |

FOREIGN PATENT DOCUMENTS

| | | | |
|---|---|---|---|
| 0327495 | 8/1989 | European Pat. Off. | 623/20 |
| 0381352 | 8/1990 | European Pat. Off. | |
| 0447065 | 9/1991 | European Pat. Off. | |
| 3314038 | 4/1983 | Fed. Rep. of Germany | |
| 3334531 | 8/1985 | Fed. Rep. of Germany | |
| 3730174 | 9/1987 | Fed. Rep. of Germany | |
| 8603117 | 6/1986 | PCT Int'l Appl. | |
| 8909579 | 10/1989 | PCT Int'l Appl. | |
| 1462876 | 4/1974 | United Kingdom | |
| 1360485 | 7/1974 | United Kingdom | 623/20 |
| 1403106 | 8/1975 | United Kingdom | |
| 1534263 | 11/1978 | United Kingdom | |
| 2219942 | 12/1989 | United Kingdom | |

OTHER PUBLICATIONS

Brochure-The GSB Knee Prosthesis.
Brochure-Microloc-The Porous Coated Knee Design.
Brochure-The CSR Uni-Condylar Knee.
Brochure-The Nuffield Total Knee.
Brochure-Mark II PCR Total Knee Replacement System.

Primary Examiner—David Isabella
Assistant Examiner—Gina Gualtieri
Attorney, Agent, or Firm—Lee, Mann, Smith, McWilliams, Sweeney & Ohlson

[57] ABSTRACT

A knee prosthesis comprises (i) a femoral component having a medial condyle and a lateral condyle and (ii) a tibial component. The rolling surface of the medial condyle is part-spherical and the tibial component has a complementary part-spherical depression in its upper surface to receive the medial condyle. The bearing surface of the lateral condyle includes a posterior part which has a curvature in a substantially sagittal plane about a first point on a transverse axis that passes through the center of curvature of the rolling surface of the medial condyle and an anterior part which has a curvature in the same plane about a point that lies on a second transverse axis parallel to, and anterior to, the first transverse axis. The tibial component has an arcuate groove to receive the lateral condyle and to permit, in flexion of the knee after implantation, limited anterior/posterior movement of the lateral side of the tibia relative to the femur. In flexion of the knee the posterior part of the rolling surface of the lateral condyle is received in this arcuate groove but, as the knee straightens and approaches its straightened condition, the anterior part of this rolling surface bears on the anterior end of the groove and thereby forces the lateral side of the tibial component to move anteriorly relative to the lateral condyle by a camming action. In this way anterior/posterior movement of the lateral side of the tibia relative to the femur is hindered in the straightened condition of the knee.

12 Claims, 3 Drawing Sheets

KNEE PROSTHESIS

This invention relates to a knee prosthesis.

Knee joints can undergo traumatic damage and can wear as a result of age, obesity, or stress. In addition they can degenerate due to chronic diseases such as osteo arthritis, rheumatoid arthritis, or inflammatory connective tissue diseases. As a result it may become necessary to implant surgically a knee prosthesis in a patient in order to improve his or her mobility, to relieve pain, to correct deformity or all three. In the course of implantation the surgeon will excise damaged or degenerated bone tissue from the end of the femur and/or from the end of the tibia and will replace it by one or more components made of a suitable physiologically acceptable inert material. In a complete knee prosthesis a femoral component or components can replace one or both of the natural condyles present on the lower end of a femur, as may be necessary; in addition a tibial part may be fitted to the upper end of the patient's tibia. Often the tibial part is made from a plastics material, such as ultra high molecular weight polyethylene, sometimes with a metal backing plate, whilst the femoral component is made from a suitable metal or alloy.

There are various methods for fixing the components in place; in some cases short pegs of metal or plastics can be used to hold the components in position, these pegs being received in corresponding cavities formed in the end of the respective bone by the surgeon in the course of the implantation operation. Metal pegs can alternatively be used. Such pegs can be integral with, or separate components from, the femoral component or the tibial component, as the case may be. Designs with relatively long locating pegs, usually of metal, are also known. In this case the locating peg may be integral with the femoral component or with the backing plate of the tibial component.

In the course of the operation the surgeon may also replace the rear surface of the patella or knee cap. Alternatively the natural patella surface can be retained.

The natural knee joint is complemented by two collateral ligaments, one on the lateral side of the joint and the other on the medial side thereof, each attached both to the tibia and to the femur. The points of attachment of the collateral ligaments to the femur are approximately on the axis of the arc along which the other end of the tibia moves and the knee flexes. In addition to the two collateral ligaments on the outsides of the knee joint, there are also two cruciate ligaments in the middle of the knee joint. One of these cruciate ligaments is attached to the posterior margin of the tibia, whilst the other is attached towards the anterior margin of the tibia. Both ligaments are attached to the femur in the notch between the condyles approximately on the axis of the collateral ligaments. Often one or both of the cruciate ligaments, particularly the anterior cruciate ligament, deteriorates or deteriorate as a result of the degeneration of the knee joint that gives rise to the need for a knee prosthesis implantation operation. Hence the surgeon may remove the anterior cruciate ligament, or both of the cruciate ligaments in the course of the implantation operation.

In a normally operative human knee-joint the flexion process basically occurs in a substantially sagittal plane, that is to say a plane substantially parallel to the median longitudinal antero-posterior plane of the body. However this flexion process involves a complex pattern of relative movements of the tibia and femur which include both lateral and rotational displacements. The former are facilitated by the hinge joint of the knee and the latter by cartilaginous menisci. These menisci are in mutual contact with both tibia and femur.

In a healthy knee, it is possible with a flexed knee to rotate the tibia axially without also rotating the femur about its axis. In this case the toes move through an arc and there is some rotation of the tibia at the knee relative to the femur. However, when the knee is straightened it becomes impossible to rotate the tibia axially without also rotating the femur about its axis at the hip.

The menisci are functionally active in this rotational moment of the knee by anterior/posterior gliding and in load distribution by modulation of the contact area through which applied load is transmitted. The rotation of the knee joint, as described above, occurs only during the flexion/extension process and, as the leg is moved towards maximum extension, the menisci glide into the fixed position and the knee locks.

The idealised prosthetic knee must be capable of reproducing both the complex articulation and the load control functions if it is successfully to permit free movement and to prevent further damage to the associated skeletal elements. These dual functions present a degree of mutual exclusivity in that, the greater is the area of surface contact giving improved load distribution, the less suitable is the system to permit mutually independent articulations.

Previous prostheses have ignored the requirement of anterior/posterior rotation in favour of a simple hinge device allowing only pivotal rotation about a single horizontal axis. Alternatively they have incorporated prosthetic menisci allowing a degree of anterior/posterior rotation or allowing unrestricted floating. These latter have involved the use of two menisci, each in mutual contact both with the metal tibial backing plate and also with a respective one of the lateral and medial condyles of the prosthetic femoral component. An example of such a knee prosthesis is that described in GB-A-1534263. Such a system, however, is subject to uncontrolled movements which do not reflect the natural pattern of articulation during the flexion process.

Another proposal, which is described in GB-A-2219942, includes a single meniscal element which is provided with inter-engaging locating means, such as a central pivot located in a shaped central cut-away, and a locating flange coacting with a recess to prevent excessive displacement while allowing limited rotary and anterior/posterior movement.

It has also been taught in EP-A-0381352 to have a modular bearing member seated within a tray element of the tibial component which includes a superiorly projecting imminence for reception between the condyle elements of the femoral component. A cam surface on a projection from the imminence is engaged during flexion and controls the degree of permitted rotation from 11° at about 90° of flexion to minimal at hyperextension.

All such prior art proposals permit rotation around the vertical central axis of the prosthesis with no functional distinction between lateral and medial condyles.

In GB-A-1403106 there is disclosed a knee joint prosthesis comprising a smooth rounded male component having two continuous curved convex condylar articulating surfaces and a female component having two mated continuous curved elongate concave articulating surfaces, the portions thereof which contact the mated male articulating surface during flexion having a radius of curvature slightly greater than that of the corresponding portions of the respective male articulating surface. In this way each pair of male and female articulating surfaces are in contact only at a substantial point of contact. Moreover in this design of joint the continuous curved elongated concave articulating surface of each female component is so shaped that, in response to the combined vector forces surrounding the joint after amputation, the male component during flexion slides thereon, continuously shifting the substantial point of contact in the longitudinal direction of the respective elongated articulating surface.

FIG. 3 of GB-A-1360485 is said to illustrate schematically the basic geometry of the knee joint which leads to the helicoidal motion of the tibia during flexion. In this Figure the lateral tibial condyle 13 is represented as a part-spherical depression and the medial tibial condyle 15 as an arcuate groove having a radius R, in the plane normal to the tibial axis. FIG. 5 of this prior art document shows that the lateral condyle 22 of the femoral replacement unit 16 is of prolate spheroidal form, i.e. it forms part of a sphere which is lengthened slightly in the anterior-posterior direction. This condylar protuberance mates with a similarly prolate spheroidal tibial lateral condylar socket 23 in the replacement joint unit of FIG. 6 of GB-A-1360845, both having an effective common mean centre of relative rotation. Although the aim is to mimic in the resulting knee joint prosthesis the natural movement of the knee, the tibial and femoral components are extremely complex in shape, requiring manufacturing by a moulding process or by powder metallurgy techniques. Such techniques are difficult to apply reliably in practice so that the costs of manufacture of reliable prostheses would be extremely high and there is a probability of a high rate of rejection at the quality control stage because of the difficulty of forming such complex shapes with the requisite accuracy of dimensions and strength.

An endoprosthetic knee joint is described in GB-A-1462876 with two femoral portions and two tibial plateaux, each having a planar semi-circular upper surface.

DE-A-3314038 discloses a knee joint prosthesis comprising a tibia component carrying a concave spherical surface and a femur component carrying a corresponding convex spherical surface permitting rotation about the joint axis. The tibia component also possesses, at a distance from the concave spherical surface, a flat zone the continuation of which cuts the concave spherical surface in a circular arc. The femur component carries a cylindrical surface partly surrounding the rotational axis and rolling on the flat surface of the tibia component.

A further proposal in DE-A-3730174 has a tibia component with flat parts complete with slide surfaces for the thigh part. An artificial hump piece is connected to the ends of artificial cruciate ligaments.

DE-A-3334531 suggests an endoprosthesis for a knee joint with the condyle support arranged on the dorsal fringe section of the tibia plateau.

Other prior art documents include US-A-3816855, US-A-3840905, US-A-4178641, US-A-4207627, US-A-4261064, US-A-4714472, US-A-4728332, US-A-4963152, EP-A-0447065, WO-A-86/03117 and WO-A-89/09759.

There are a number of devices that have been marketed including:

(a) The CSR Uni-Condylar Knee sold by Corin Medical Limited, Chesterton Lane, Cirencester, Gloucestershire GL7 1YL, England;

(b) The Nuffield Total Knee, also sold by Corin Medical Limited;

(c) The Mark II PCR Total Knee Replacement System, sold by Protek AG, P.O. Box 2016, CH-3001 Berne, Switzerland;

(d) The Miller/Galente Porous Tivanium Total Knee System, sold by Zimmer, Inc., P.O. Box 708, Warsaw, IN 46580, U.S.A.;

(e) The PCA Unicompartmental Knee System, sold by Howmedica, a division of Pfizer Hospital Products Group, Inc., 359 Veterans Boulevard, Rutherford, N.J. 07070, U.S.A.;

(f) The GSB-knee prosthesis sold by Allo Pro GmbH, Dorstener Strasse 27, D-4650 Gelsenkirchen, Germany; and (g) The Microloc Porous Coated Knee System sold by Johnson & Johnson Products Inc., Orthopaedic Division, New Brunswick, N.J. 08903, U.S.A.

There is a need to provide a knee prosthesis which mimics more accurately after implantation the natural movements of a healthy knee. There is a further need to provide such a knee prosthesis whose femoral component can be produced from a metal blank by conventional machining operations. There is also a need to provide a knee prosthesis whose femoral component has relatively simple geometry, permitting its production reliably by machining techniques, and which mimics the movement of the natural knee joint, following implantation.

The present invention accordingly seeks to provide an improved knee prosthesis which will allow the patient to move his knee substantially in the same manner as though he had not had to undergo implantation of a knee prosthesis.

According to the present invention there is provided a knee prosthesis comprising:

(a) a femoral component having (i) a medial condyle with a substantially part-spherical rolling surface and (ii) a lateral condyle with a rolling surface including a posterior part having a curvature in a substantially sagittal plane about a first point on a transverse axis that passes through the centre of curvature of the rolling surface of the medial condyle and an anterior part having a curvature in the same substantially sagittal plane about a point that lies on a second transverse axis parallel to the first transverse axis; and (b) a tibial component having (i) a substantially part spherical concave medial bearing surface for receipt of, and complementary to, the rolling surface of the medial condyle and (ii) an arcuate groove providing a lateral bearing surface for the rolling surface of the lateral condyle and permitting, after implantation of the knee prosthesis, limited anterior/posterior movement of the lateral side of the tibia relative to the femur in flexion of the knee joint, the posterior part of the rolling surface of the lateral condyle being arranged to bear on the lateral bearing surface in flexion of the knee, and the anterior part of the rolling surface of the lateral condyle being arranged to enter the arcuate groove as the knee approaches its straightened condition, thereby to force the lateral side of the tibial component to move anteriorly relative to the lateral condyle by a camming action and to hinder anterior/posterior movement of the lateral side of the tibia relative to the femur in the straightened condition of the knee.

Preferably the femoral component further has a patella track which is offset towards the lateral condyle throughout its articulation but particularly in flexion.

The condyles have a common transverse generator axis and the patella track preferably extends substantially at 90° to said common transverse generator axis.

The medial condyle of the femoral component is preferably larger than the lateral condyle and has a surface portion which is substantially part-spherical. The lateral condyle is typically smaller than the medial condyle and has a surface portion which is part-toroidal.

The lateral bearing surface of the tibial component preferably describes an arc, the centre of which coincides with the lowermost point of the substantially part-spherical medial bearing surface. At its posterior end the lateral bearing surface is preferably shaped to allow a rolling or a sliding movement of the lateral condyle. However, towards its anterior end, the lateral bearing surface may slope upwardly so as to tend to force the lateral condyle to track towards the posterior of the lateral bearing surface as the patient extends his knee. In this way the knee can be made to lock as the leg moves closer towards the extended position. In addition the radius of curvature of the lateral condyle can vary in an anterior/posterior plane, increasing towards the upper end of the condyle.

The posterior part and the anterior part of the rolling surface of the lateral condyle may each include in profile a part-cylindrical surface, Such a part-cylindircal surface may be bounded in profile in each case on each side with rounded shoulders. Conveniently the radius of curvature of the bearing surface of the medial condyle lies in the range of from about 20 mm to about 32 mm.

In one preferred embodiment the radii of curvature of the arcs in a substantially sagittal plane of the posterior and anterior parts of the rolling surface of the lateral condyle are substantially the same. In one arrangement the second transverse axis is anterior to the first transverse axis and the first transverse axis and the second transverse axis are arranged so that, in the straightened condition of the knee after implantation, they lie in a substantially horizontal plane.

Alternatively the radius of curvature of the anterior part of the rolling surface of the lateral condyle in a substantially sagittal plane is larger than the radius of curvature of the posterior part of the rolling surface of the lateral condyle in that substantially sagittal plane. The radii of curvature of the arcs in a substantially sagittal plane of the posterior and anterior parts of the rolling surface of the lateral condyle may each lie in the range of from about 16 mm to about 25 mm.

Typically the femoral component is made from a physiologically acceptable metal or alloy, while at least the medial condyle and the lateral condyle of the femoral component are preferably highly polished. Normally the tibial component comprises a physiologically acceptable plastics material.

In order that the invention may be clearly understood and readily carried into effect, two preferred embodiments thereof will now be described, by way of example only, with reference to the accompanying drawings, wherein.

Referring to FIGS. 1 to 4 of the drawings, a knee prosthesis for implantation in the left leg of a patient comprises a femoral component 1 and a tibial component or meniscus 2. Femoral component 1 is preferably made from a physiologically acceptable metal, such as a CoCr alloy, a CoCrMo alloy, a CoNiCrMo alloy, Ti or a Ti alloy, whilst tibial component or meniscus 2 is made from a suitable plastics material, such as ultra high molecular weight polyethylene.

A knee prosthesis for implantation in the right leg of a patient is a mirror image of the knee joint prosthesis of FIGS. 1 to 4.

Femoral component 1 can be provided in known manner with one or more integral or separate anchorage pegs (not shown) for reception in prepared cavities in the femur of the patient in order to locate it securely in place, with or without the use of cement, as the surgeon prefers. The tibial component or meniscus 2 can be used in conjunction with a horizontal backing plate, which can also be fitted with an integral locating peg; such a metal backing plate (not shown) can be secured to the upper end of the patient's tibia in conventional manner and secured thereto, as required, with one or more pegs (not shown) either integral with, or separate from, the tibial component 2. The anchorage pegs used to secure the femoral component and the metal backing plate in place may be made from metal or plastics, as desired or as may be most expedient.

Tibial component 2 may be fixedly secured to the metal backing plate. Alternatively it may be mounted with a limited degree of floating movement relative to a metal backing plate (not shown).

Figure 1:
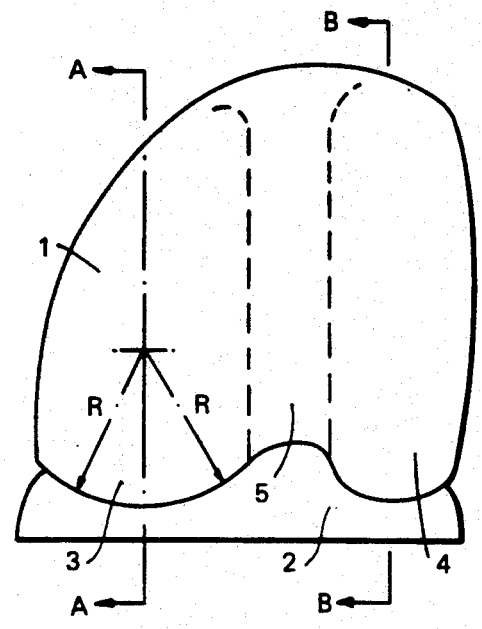
FIG. 1 is a front view of a knee joint prosthesis constructed in accordance with the invention for implantation in the left knee of a patient.

As can be seen from FIG. 1, the femoral component 1 is asymmetric, the medial condyle 3 being larger than the lateral condyle 4, with a laterally offset patella track 5 delineating the medial condyle 3 and the lateral condyle 4. These condyles 3 and 4 are preferably highly polished. The medial condyle 3 has a surface portion which is largely spherical and is shaped to be substantially congruent with a spherical concave depression 6 in the tibial component or meniscus 2. The lateral condyle 4 is rounded but is shaped to form an incongruent contact with a trough-shaped depression 7 in the tibial component or meniscus 2. Lateral condyle 4 may have a surface portion which is substantially part-toroidal in shape.

The groove of the patella track 5 runs in a plane which is at 90° to the generator axis 8 of the condyles 3 and 4. This generator axis 8 also lies substantially on the horizontal hinge axis of the knee joint.

Figure 2:
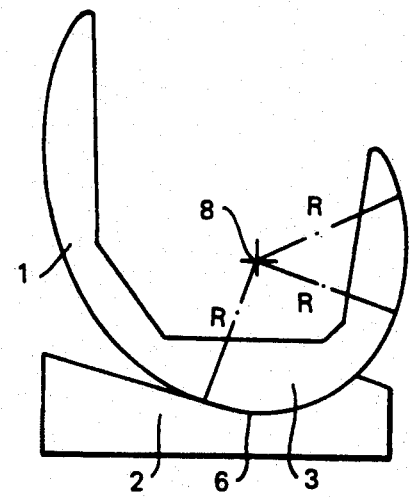
FIG. 2 is a vertical section on the line A—A of FIG. 1 through the medial side of the knee prosthesis corresponding to the leg being at full extension.

The radius of curvature R of the spherical depression 6 corresponds to the radius R of the medial condyle 3 both laterally (as indicated in FIG. 1) and in an anterior/posterior plane (as shown in FIG. 2).

Figure 3:
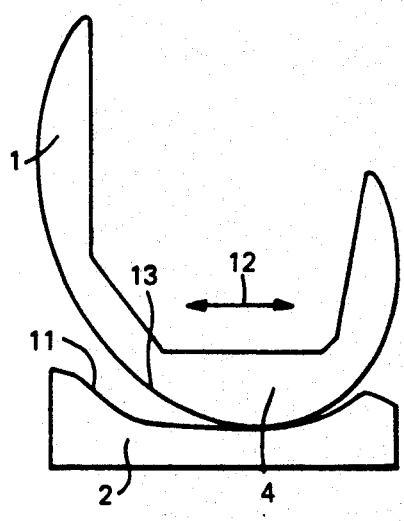
FIG. 3 is a similar vertical section on the line B—B of FIG. 1 through the lateral side of the knee joint prosthesis.
Figure 4:
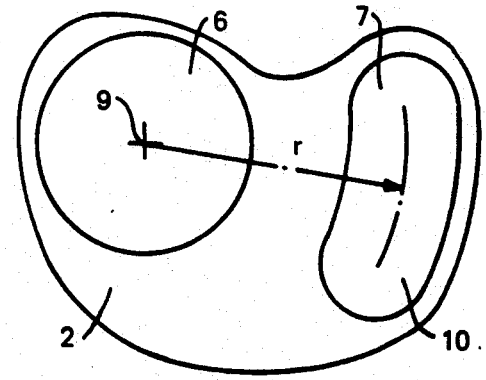
FIG. 4 is a top plan view of the tibial component of the knee joint prosthesis of FIGS. 1 to 3.

The tibial component or meniscus 2, as can be seen in FIG. 4, has an upper surface with the two concave depressions 6 and 7 situated to engage their respective femoral condyles 3 and 4. The lateral depression 7 forms an arc-shaped curve in plan view which has as the centre point of the arc the centre point 9 of depression 6. The arc of the arcuate bottom 10 of groove 7 has a radius r. The construction of the tibial component 2 is thus totally different from the arrangement shown in FIG. 3 of GB-A-1360485 in which it is the lateral tibial condyle that is part-spherical while the medial condyle is an arcuate groove.

As can be seen from FIG. 3 of the drawings, the bottom of groove 7 is relatively flat and permits relative rotation between the tibia and the femur about the axis 9. During this rotational movement lateral condyle 4 can slide along track 7. However, towards the anterior end of track 7 it slopes upwardly, as indicated at 11 in FIG. 3. In addition the anterior surface of lateral condyle 4 has a somewhat larger radius of curvature than the radius of curvature where it slides (as indicated by the arrow 12 in FIG. 3) and rotates in groove 7. As the knee approaches the straightened position, so the portion 13 of larger radius of curvature comes into contact with the slope 11, thereby forcing femoral component 11 to slide posteriorly in the track 7, thereby locking the knee joint against relative rotation between the tibia and femur. Thus the shape of the slope 11 at the anterior end of the arcuate lateral depression 7 can be designed to allow anterior/posterior movement in flexion (as indicated by the arrow 12 in FIG. 3) up to about 10° of full extension, then over the last 10° to allow the tibia to move fully to the anterior and lock the knee against rotation, so that the tibia can only rotate about its axis if the femur also rotates about its axis.

The congruent nature of the contact between the medial condyle 3 and the tibial component or meniscus 2 allows an improved load distribution pattern and acts as a stable pivot for rotation of the knee when in flexion. Rotation is limited by the anterior/posterior tracking of the lateral condyle 4 through the arc described by the lateral trough 7. This anterior/posterior tracking may occur during flexion or extension except over the last 10° or so of extension, whereas during the last 10° of extension or so the femur will slide fully posterior on the tibia with minimum rotational ability and full extension. In this way a close approach to the natural movement of the knee can be achieved in this embodiment of the knee prosthesis of the invention.

Figure 7:
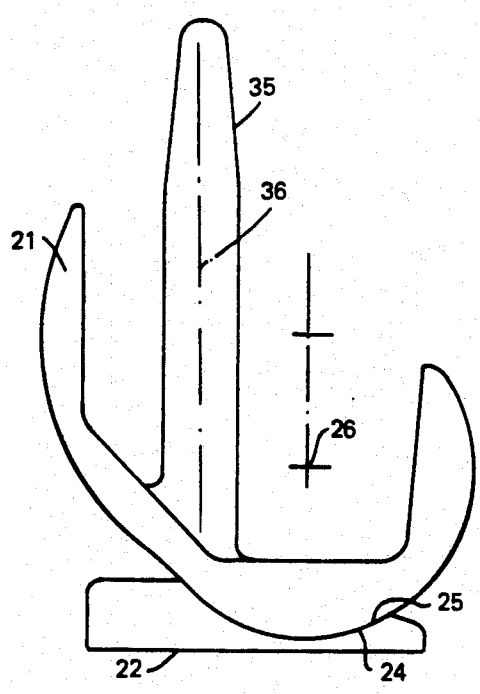
FIG. 7 is a section in a sagittal plane on the line X—X of FIGS. 5 and 6.

The knee prosthesis of FIGS. 4 to 8 includes a femoral component 21 and a tibial component 22. Preferably femoral component 21 is made from a physiologically acceptable metal while tibial component 22 is constructed from a suitable plastics material, of which ultra high molecular weight polyethylene is a typical example. Tibial component 22 may be screwed in place on the upper end of a patient's tibia after resection thereof. Alternatively tibial component 22 can be secured to the upper end of a metal component (not shown) of conventional design implanted in the upper end of the patient's resected tibia. It has a part-spherical depression 23 in its upper face 24 which provides a concave bearing surface for the medial condyle 25 of the femoral component 21. As shown in FIG. 7 the medial condyle 25 is part-spherical, its centre of curvature lying on a transverse axis 26 which corresponds to the centre line of the natural condyles of the patient's femur and which constitutes the effective hinge axis of the knee.

The upper face 24 of the tibial component 22 is also formed towards its lateral side with an arcuate groove 27, the centre line 28 of which describes an arc about the bottom point 29 of depression 23. Groove 27 provides a track for the lateral condyle 30 of femoral component 21 and permits, in flexion of the knee after implantation, a limited amount of anterior-posterior movement of the lateral side of the tibia relative to the patient's femur. Hence, in flexion of the knee, the tibia can twist through a limited range of movement about the axis of the tibia. As can be seen from FIG. 8, the posterior part 31 of the rolling surface of the lateral condyle 30 (i.e. the right-hand side as viewed in FIG. 8) is arcuate in section, the centre of curvature lying on the transverse axis 26. The anterior part 32 of the rolling surface of the lateral condyle is also arcuate in section; however, the centre of curvature of the anterior part 32 lies on a second transverse axis 33 which is parallel to, and anterior to, the first mentioned transverse axis 26. In the straightened condition of the knee prosthesis, as illustrated in FIG. 8, the two axes 26 and 33 lie substantially in a common horizontal plane.

Between medial condyle 25 and lateral condyle 30 is a patella groove 34; this is axially straight, the axis of this groove also lying in a substantially sagittal plane. Femoral component 21 is further provided with a stem 35 whose centre line 36 is indicated in FIG. 5.

Figure 5:
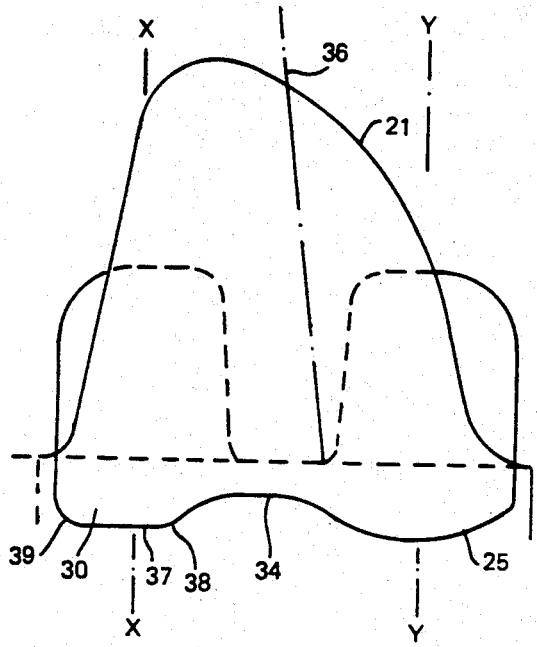
FIG. 5 is a front view of a femoral component of a second embodiment of a knee prosthesis according to the invention for implantation in the right knee of a patient.
Figure 6:
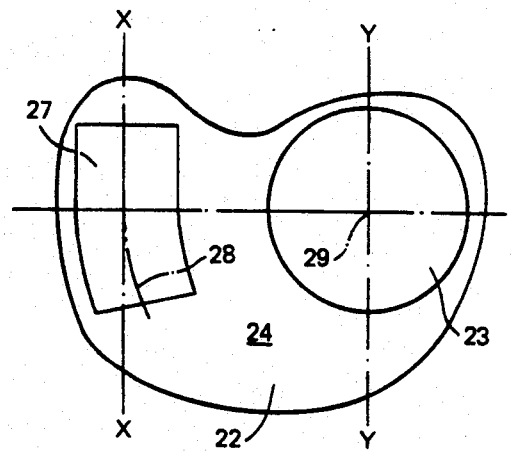
FIG. 6 is a top plan view of the tibial component of the second embodiment.
Figures 8, 9:
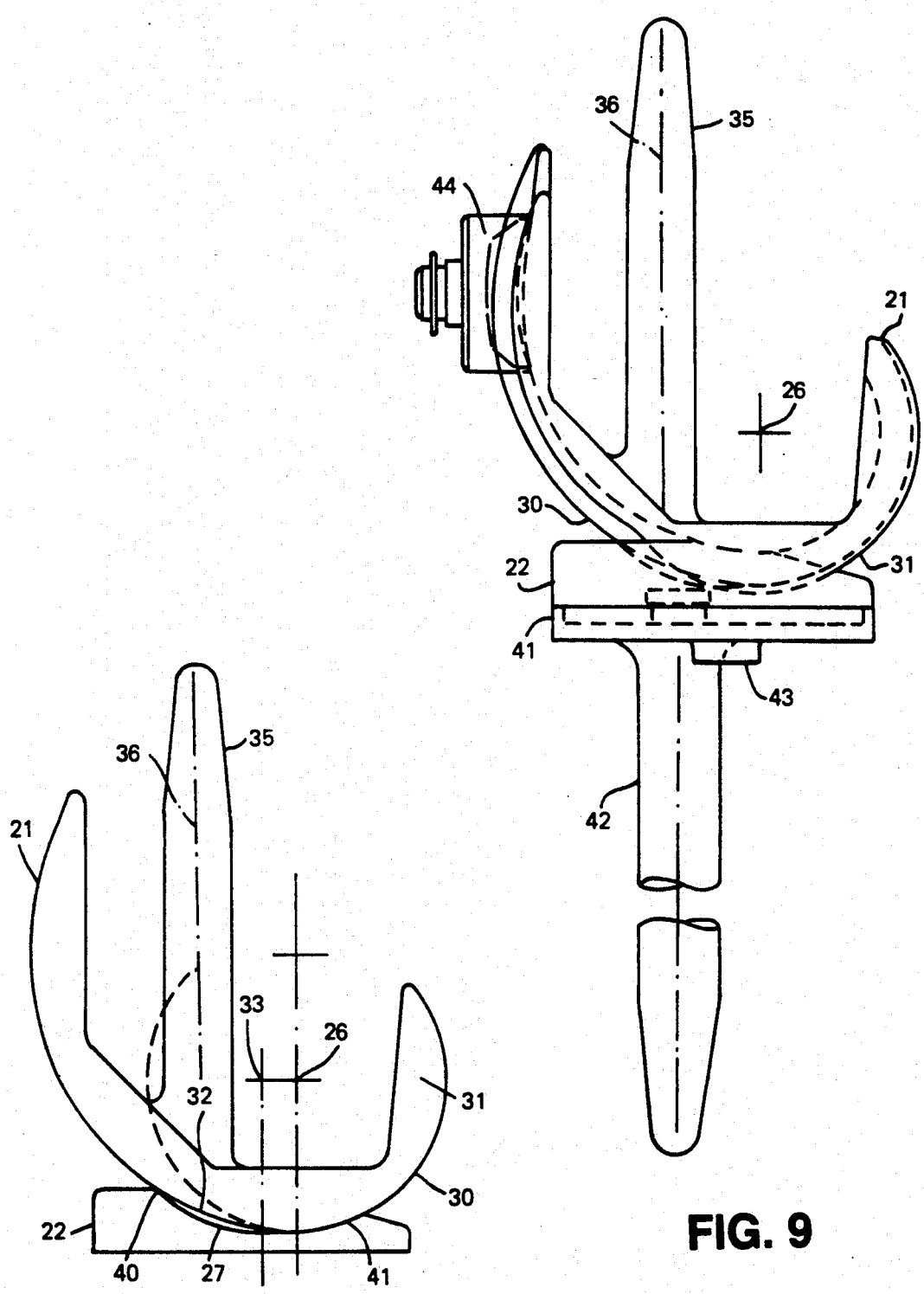
FIG. 8 is a section in a sagittal plane on the line Y—Y of FIGS. 5 and 6.
FIG. 9 is a side view of a third embodiment of knee prosthesis according to the invention, also for implantation in the right knee of a patient.

In cross section in a plane substantially perpendicular to the sagittal plane of FIGS. 7 and 8, as can be seen from FIG. 5, the profile of each of the two parts 31 and 32 of the rolling surface of the lateral condyle 30 includes a part-cylindrical portion 37 centred on one or other of the two transverse axes 26 and 33, flanked by rounded shoulders 38 and 39. Groove 27 has a complementary profile.

FIG. 8 shows the knee prosthesis with the leg in straightened condition. In this case the anterior part 32 of the rolling surface of the medial condyle 30 bears on the anterior end 40 of groove 27, thus forcing the lateral side of the tibial component 22 to move forwardly by a camming action and forcing the first part 31 of the rolling surface of lateral condyle 30 to move on the posterior end 41 of groove 27. However, as the knee flexes, so axis 36 rotates clockwise relative to the tibial component 22 (as shown in FIG. 8), the anterior part 32 of the rolling surface of the lateral condyle 30 moves out of the groove 27 and the posterior part 31 moves into the groove 27. As the camming action is reduced by reason of the anterior part 32 moving out of the groove 27, so lateral condyle 30 is able to slide in groove 27 and axial rotation of the tibia relative to the femur becomes possible. Upon straightening the leg from the flexed position, initially posterior part 31 of the rolling surface of the lateral condyle 30 bears in groove 27 and can slide therein. However, as the knee straightens more and more from the flexed position so the anterior part 32 of the rolling surface begins to contact the front end 40 of groove 27, thereby forcing the lateral side of the tibial component forward and causing posterior part 31 of the rolling surface of lateral condyle 30 to move rearwardly in the groove 27.

Preferably femoral component 21 is highly polished. If desired, stem 35 can be omitted.

The arcuate lengths of the posterior and anterior parts 31 and 32 of the rolling surface of the lateral condyle 30 in the respective sagittal plane are desirably selected so that, at least over the last 10° or so of bending of the knee from its flexed position to the straightened condition of FIGS. 7 and 8 the anterior part 32 is exerting its camming action sufficiently to force the posterior part 31 towards the rearward end of slot 27, thereby preventing twisting of the tibia about its axis relative to the femur.

In a typical knee prosthesis according to the invention the radius of curvature of the part-spherical rolling surface of the medial condyle 25 is from about 20 to about 32 mm, e.g. about 25 mm. On the other hand the radius of curvature of the axis in a substantially sagittal plane of the posterior and anterior parts 31 and 32 of the lateral condyle 30 are preferably the same as each other and typically smaller, e.g. in the range of from about 16 to about 25 mm, e.g. about 19 mm. Typically axis 33 is offset forwardly of axis 26 by a distance of from about 4 to about 8 mm, e.g. about 5.1 mm. This distance is fixed by the cam shape of the anterior part 30 at full extension (i.e. as shown in FIG. 8) and by the height of point 40 above the bottom of groove 27. The more anterior the position of point 40 is, the bigger will be the distance between axes 26 and 33. Moreover, although it is shown in FIG. 8 that axes 26 and 33 lie in a common horizontal plane in the straightened condition of the leg, this is not essential. Thus axis 33 can lie slightly above or below this horizontal plane, although preferably no more than 1-2 mm off this plane.

FIG. 9 shows a side view of a further embodiment of knee prosthesis with a tibial implant 22 on a metal backing plate 41 with a stem 42 and a locating stud 43. Reference numeral 44 indicates a patella component which is secured to the rear of the patient's patella and runs in the patella groove 34. Tibial component 22 is otherwise essentially identical to that of FIGS. 5 to 8, while femoral component 21 is the same as in FIGS. 5 to 8.

We claim:

1. A knee prosthesis for implantation in a knee joint of a leg of a patient, said leg including a femur having a lateral side and a medial side and a tibia having a lateral side and a medial side, and said knee prosthesis comprising:
   a. a femoral component for implantation in the femur of the patient to form one part of a knee joint, said femoral component having (i) a medial condyle with a substantially part-spherical rolling surface having a centre of curvature and (ii) a lateral condyle with a rolling surface including a posterior part having a curvature in a substantially sagittal plane about a first point on a transverse axis that passes through the centre of a curvature of the rolling surface of the medial condyle and an anterior part having a curvature in the same substantially sagittal plane about a point that lies on a second transverse axis parallel to the first transverse axis; and
   b. a tibial component for implantation in the tibia of the patient to form another part of a knee joint, said tibial component having (i) a substantially part-spherical concave medial bearing surface for receipt of, and complementary to, the rolling surface of the medial condyle, the medial condyle of the femoral component being substantially congruent with the medial bearing surface of the tibial component, and (ii) an arcuate groove providing a lateral bearing surface for the rolling surface of the lateral condyle and permitting, after implantation of the knee prosthesis in the patient, limited anterior/posterior movement of the lateral side of the tibia relative to the femur in flexion of the knee joint, the posterior part of the rolling surface of the lateral condyle being arranged to bear on the lateral bearing surface in flexion of the knee, and the anterior part of the rolling surface of the lateral condyle being arranged to enter the arcuate groove as the knee approaches its straightened condition, thereby to force the lateral side of the tibial component to move anteriorly relative to the lateral condyle by a camming action and to hinder anterior/posterior movement of the lateral side of the tibia relative to the femur in the straightened condition of the knee.

2. A knee prosthesis according to claim 1, in which the posterior part and the anterior part of the rolling surface of the lateral condyle each include in profile a part-cylindrical surface.

3. A knee prosthesis according to claim 2, in which the part-cylindrical surface is bounded in profile in each case on each side with rounded shoulders.

4. A knee prosthesis according to claim 1, in which the radius of curvature of the bearing surface of the medial condyle lies in the range of from about 20 mm to about 32 mm.

5. A knee prosthesis according to claim 1, in which the radii of curvature of the arcs in a substantially sagittal plane of the posterior and anterior parts of the rolling surface of the lateral condyle are substantially the same.

6. A knee prosthesis according to claim 5, in which the second transverse axis is anterior to the first transverse axis and in which the first transverse axis and the second transverse axis are arranged so that, in the straightened condition of the knee after implantation, they lie in a substantially horizontal plane.

7. A knee prosthesis according to claim 1, in which the radius of curvature of the anterior part of the rolling surface of the lateral condyle in a substantially sagittal plane is larger than the radius of curvature of the posterior part of the rolling surface of the lateral condyle in that substantially sagittal plane.

8. A knee prosthesis according to claim 1, in which the radii of curvature of the arcs in a substantially sagittal plane of the posterior and anterior parts of the rolling surface of the lateral condyle each lie in the range of from about 16 mm to about 25 mm.

9. A knee prosthesis according to claims 1, in which the femoral component is made from a physiologically acceptable metal or alloy.

10. A knee prosthesis according to claim 9, in which at least the medial condyle and the lateral condyle of the femoral component are highly polished.

11. A knee prosthesis according to claim 1, in which the tibial component comprises a physiologically acceptable plastics material.

12. A knee prosthesis according to claim 1, in which the femoral component is formed with a patella track between the medial and lateral condyles with an axis that lies in a substantially sagittal plane.

* * * * *